(12) United States Patent
Romeo

(10) Patent No.: US 10,424,033 B2
(45) Date of Patent: Sep. 24, 2019

(54) HEALTHCARE PRACTICE MANAGEMENT SYSTEMS AND METHODS

(71) Applicant: Breg, Inc., Carlsbad, CA (US)

(72) Inventor: Steven Robert Romeo, Encinitas, CA (US)

(73) Assignee: Breg, Inc., Carlsbad, CA (US)

( * ) Notice: Subject to any disclaimer, the term of this patent is extended or adjusted under 35 U.S.C. 154(b) by 0 days.

(21) Appl. No.: 13/843,031

(22) Filed: Mar. 15, 2013

(65) Prior Publication Data

US 2014/0278535 A1  Sep. 18, 2014

(51) Int. Cl.
| | | |
|---|---|---|
| *G06Q 50/22* | (2018.01) | |
| *G06Q 10/10* | (2012.01) | |
| *G06F 19/00* | (2018.01) | |
| *G16H 40/20* | (2018.01) | |

(52) U.S. Cl.
CPC ........... *G06Q 50/22* (2013.01); *G06F 19/328* (2013.01); *G06Q 10/1095* (2013.01); *G16H 40/20* (2018.01)

(58) Field of Classification Search
CPC .... G06Q 50/22; G06Q 10/1095; G06Q 50/24; G06F 19/327
USPC ........................................................ 705/2, 3
See application file for complete search history.

(56) References Cited

U.S. PATENT DOCUMENTS

| | | | |
|---|---|---|---|
| 2003/0050802 A1* | 3/2003 | Jay et al. ........................... | 705/3 |
| 2006/0293572 A1* | 12/2006 | Bulat ................... | A61B 5/0002 600/300 |
| 2008/0262867 A1* | 10/2008 | Bayne et al. ..................... | 705/2 |
| 2009/0138283 A1* | 5/2009 | Brown ................. | G06Q 10/109 705/3 |
| 2010/0299155 A1* | 11/2010 | Findlay et al. ................... | 705/3 |
| 2010/0305966 A1* | 12/2010 | Coulter et al. .................... | 705/2 |
| 2010/0324922 A1* | 12/2010 | Kendall ................ | G06Q 50/22 705/2 |
| 2011/0093292 A1* | 4/2011 | Hussam ................ | G06F 19/363 705/3 |
| 2011/0246226 A1* | 10/2011 | Green et al. ...................... | 705/2 |
| 2013/0060577 A1* | 3/2013 | DeBusk et al. ................... | 705/3 |

* cited by examiner

*Primary Examiner* — Jonathan Ng
*Assistant Examiner* — Rachelle L Reichert
(74) *Attorney, Agent, or Firm* — Thomas A. Runk; Brooks Kushman P.C.

(57) ABSTRACT

Healthcare practice management systems and methods can be provided for managing the data flow and operation of healthcare practices. One or more applications running on client devices can be provided to facilitate the sharing of information between data storage repositories and the healthcare practice. For example, data stored in multiple different data storage systems can be retrieved and provided to the applications in a unified fashion. Likewise, data in different formats, data stored with different encryption protocols and otherwise disparate data types can be gathered, translated, and presented to the applications in a form and format readable by the application.

10 Claims, 11 Drawing Sheets

HEALTHCARE PRACTICE MANAGEMENT SYSTEMS AND METHODS

TECHNICAL FIELD

The disclosed technology relates generally to the healthcare industry, and more particularly, some embodiments relate to systems and methods for healthcare practice records management.

DESCRIPTION OF THE RELATED ART

While computers and computerized systems have found their way into most of today's businesses, some sectors are more automated than others. For example, certain sectors of the healthcare industry have been slow to automate their systems and procedures, or have yet to evolve into an integrated, user-friendly computerized solution. This is true, for example, with a number of small healthcare practices, family practices, and hospital systems in this country and around the world. However, this shortcoming is not unique to small healthcare practices and indeed, many large healthcare practices suffer from a lack of proper automation and recordkeeping. For example, some computerized systems in use today generate multiple system-to-patient interactions, using different data management systems each having different interfaces to the healthcare provider and the patient. Electronic health records, scheduling information and billing information may be stored, tracked, and maintained separately without an integrated approach to delivering this information to the healthcare provider or their patients. This can lead to errors and efficiency with the data management systems.

BRIEF SUMMARY OF EMBODIMENTS

According to various embodiments of the disclosed technology, a healthcare practice management system can be provided to assist managing the data flow and operation of healthcare practices. In some embodiments, one or more applications running on client devices can be provided to facilitate the sharing of information between data storage repositories and the healthcare practice. For example, data stored in multiple different data storage systems can be retrieved and provided to the applications in a unified fashion. Likewise, data in different formats, data stored with different encryption protocols and otherwise disparate data types can be gathered, translated, and presented to the applications in a form and format readable by the application. Encryption or other security measures can be employed to ensure data privacy is maintained to the appropriate standards.

The one or more applications can be configured to receive this information and use it in the management of the healthcare practice. For example, patient-scheduling information, patient billing information, and patient electronic health records can be retrieved from the respective storage locations and deliver to the applications in a form and format that usable by the applications. This information can be used to develop a patient schedule for the healthcare practice. The schedule can be built as a daily, weekly, or biweekly schedule, or can be built to a different timescale. The schedule can include an identification of appointment times and patients corresponding to each appointment time. Where multiple physicians or other practitioners are involved in the healthcare practice, the schedule can also indicate which physician or physicians are scheduled to see which of patients. Likewise, other resources needed for the schedule appointments can be identified for each appointment. For example, wherein appointment requires laboratory or other tests, those tests can be identified and associated with the appointment. Where special facilities, such as an operating room, for example, are required, those facilities can also be flagged and associated with a schedule appointment.

Accordingly, the one or more applications can be configured to present the scheduling information to the healthcare practitioners to facilitate management and operation of the healthcare practice. Schedules can be sorted by physician, treatment type, treatment facilities, or other resources as may be appropriate. Healthcare practitioners may be permitted to view the schedules and click on schedule entries to retrieve additional information about the scheduled appointment or the patient. For example, clicking on a schedule entry can cause the application to retrieve information, such as, for example, patient healthcare records of the patient scheduled for that appointment, billing information for that patient, resources scheduled to be used for that appointment (e.g., a particular treatment rooms, test equipment, etc.) and the like.

The application can further allow the healthcare practitioners to enter information relevant to the scheduled appointment. For example, upon examining a patient, the application can provide the ability for the healthcare practitioner to enter information about the examination or treatment provided. As a further example, the healthcare practitioner may enter data regarding a diagnosis made of the patient, actions performed during the patient's visit, prescribed medications for the patient, recommended courses of action for the patient, follow-up tests or examinations, recommended treatments, and so on.

Where equipment is prescribed to the patient (e.g., a knee brace), the equipment prescription can be entered into the application and accepted by the application. The application can be configured to provide prescription information to another healthcare practitioner who is designated to retrieve the prescribed equipment from inventory and fit the prescribed equipment to the patient. Once equipment is fitted to the patient, the healthcare practitioner can enter that information into the application, and the application can update the inventory records as well as the patient's healthcare records. Likewise, billing information can be updated to reflect delivery of a billable item to the patient.

The healthcare practice management system can also be used to track, maintain and update other patient information such as, for example, the check-in and checkout of patients for appointments, insurance and co-pay information, patient personal information, and other information useful in the care and treatment of patients.

In some embodiments, a non-transitory computer readable medium including executable instructions is provided, the executable instructions being executable by a processor in a hand-held computing device to perform a method, the method including: receiving a set of records, the records including patient identification for a plurality of patients scheduled for to visit a healthcare practice; building a schedule, the schedule showing the patient identifications for the plurality of patients scheduled and an appointment time corresponding to each patient; displaying the schedule on the hand-held computing device, wherein the schedule is sorted based on a sort order, accepting a first user input from a health care practitioner, the first user input selecting a patient or a selected patient's corresponding appointment, and providing to the health care practitioner additional information corresponding to the selected patient, wherein the additional information can include a health record of the selected patient; accepting a second user input from a health care practitioner, the second user input entering treatment information, the treatment information including information pertaining to an examination of the selected patient by the health care practitioner, accepting a third user input from a health care practitioner, the third user input entering prescription information for the selected patient; updating the records for the selected patient, the updates including the treatment information and the prescription information entered by a health care professional; accepting fourth user input confirming fulfillment of the prescription; and sending the updated records to update a central file repository. The records received can include records received from a data repository configured to store records for a plurality of patients. The records can include at least one of patient electronic health records, patient management system records; and patient billing system records. The records further can include data relating to an outcome of prescribed follow-on care.

In some embodiments, the schedule can be sorted by a resource attributed to that schedule and displayed on the hand-held computing device can be sorted by attending physician, appointment time, or treatment room. Displaying the schedule and accepting the first user input can include displaying appointment items in the schedule as linked elements on the display, and wherein the linked elements are associated with a link to the additional information corresponding to the patient. The information corresponding to the patient can include information included in the records.

The information included in the records can include at least one of patient electronic health records, patient-management-system records; and patient billing system records. Further, the treatment information can include a patient diagnosis. In various embodiments, the prescription information entered by the healthcare professional can include a prescription for an orthopedic brace or other item stocked in inventory by the healthcare practice and the method can include updating records of the inventory upon receipt of fourth user input confirming fulfillment of the prescription.

In further embodiments, a non-transitory computer readable medium including executable instructions is provided, the executable instructions being executable by a processor in a client computing device to perform a method, the method including: receiving a set of records, the set of records including patient identification for a plurality of patients scheduled for appointments at a healthcare facility in a time window; displaying a schedule on a display of the hand-held computing device, the displayed schedule including a listing of entries for a subset of the appointments scheduled at the healthcare facility in the time window; linking a schedule entry for a first appointment to a subset of the set of records that corresponds to a patient associated with the first appointment; displaying the subset of records to a healthcare practitioner in response to a request from the healthcare practitioner for that subset of records; and accepting from the healthcare practitioner an order for a prescribed item for the patient associated with the first appointment.

In some embodiments, the method can further include creating an order record, the order record including information about the order for the prescribed item, wherein the order is displayed to a second healthcare practitioner on a second client device, informing the second healthcare practitioner to provide the prescribed item to the patient associated with the first appointment; and wherein the second client device creates or updates a record indicating that the prescribed item has been delivered.

The method can also include accepting from the healthcare practitioner input confirming delivery of the prescribed item to the patient associated with the first appointment. In addition, the method can include updating inventory records to reflect that the prescribed item has been removed from inventory, and creating a patient billing record to reflect that the prescribed item has been delivered to the patient associated with the first appointment.

The method might also include accepting treatment information entered by the healthcare practitioner, the treatment information including information pertaining to an examination of the patient associated with the first appointment by the healthcare practitioner.

In still further embodiments, a system in a medical office for managing a records associated with a plurality of patients, each patient being scheduled for an appointment at the medical office is provided. In some embodiments, the system, may include: a first client computing device having a first processor, a first user interface, and a first non-transitory computer readable medium including executable instructions, the executable instructions being executable by the first processor to perform a first method; a second client computing device having a second processor, a second user interface, and a second non-transitory computer readable medium including executable instructions, the executable instructions being executable by the second processor to perform a second method. The first method can include: linking a schedule entry for a first appointment to a subset records that corresponds to a patient associated with the first appointment; displaying the subset of records to a healthcare practitioner in response to a request from the healthcare practitioner for that subset of records; and accepting from the healthcare practitioner an order for a prescribed item for the patient associated with the first appointment. The second method can include: accepting a third user input from a health care practitioner, the third user input entering prescription information for the selected patient; updating the records for the selected patient, the updates including the treatment information and the prescription information entered by a health care professional; accepting fourth user input confirming fulfillment of the prescription; and sending the updated records to update a central file repository. In addition, the first method can include displaying a schedule including the schedule entry on a display of the hand-held computing device, the displayed schedule including a plurality of entries for a subset of appointments scheduled at the healthcare facility.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The technology disclosed herein is directed toward systems and methods for healthcare practice management, data integration and automation. According to various embodiments, various aspects of a healthcare practice can be automated, and data shared amongst the several components and systems within and external to the healthcare practice. For example, patient and resource scheduling, records updating, billing and reporting can be automated.

Figure 1:
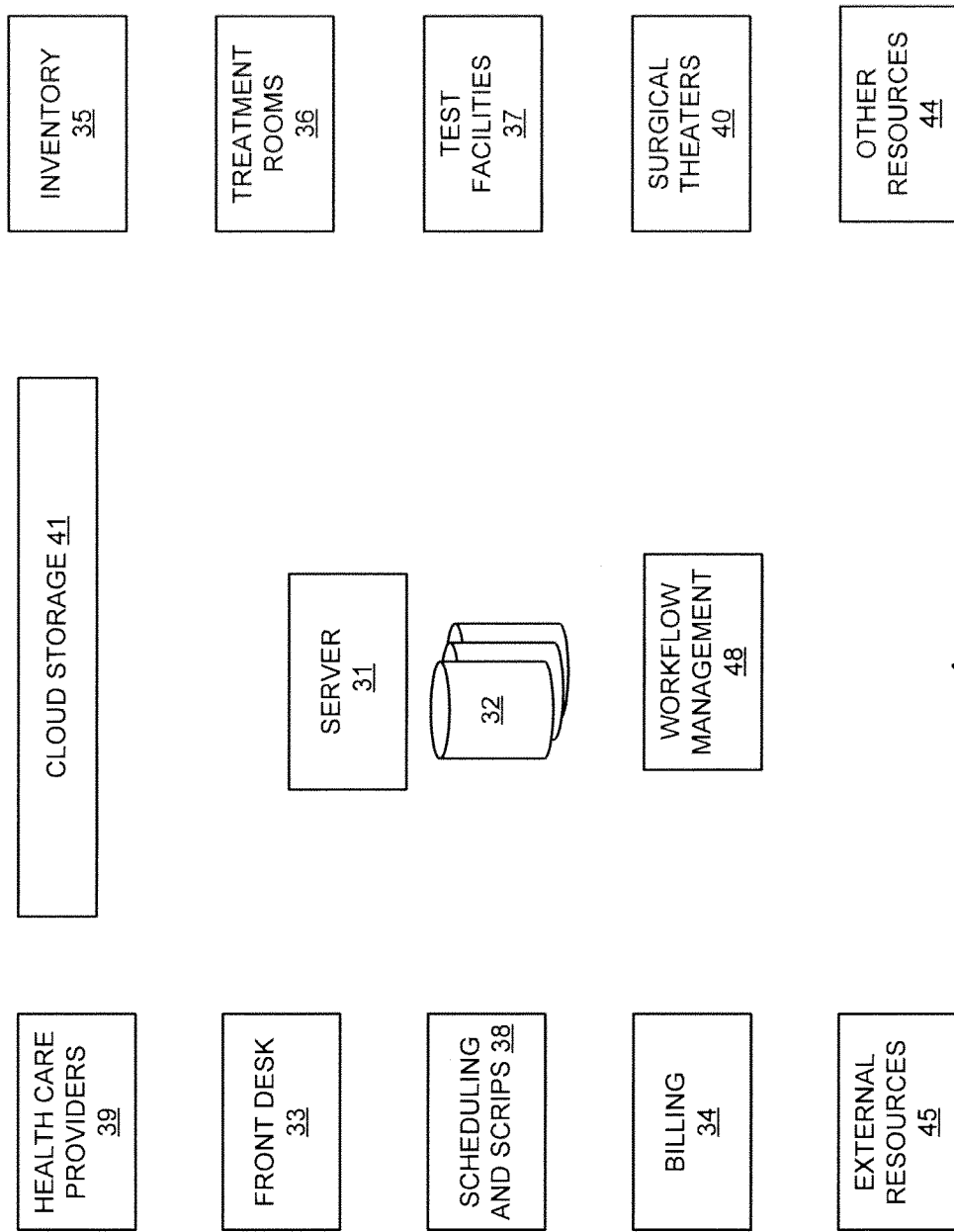
FIG. 1 is a diagram illustrating an example of a healthcare practice with which the disclosed technology may be implemented in accordance with one embodiment.

Before describing the technology in detail, it is useful to describe an example environment in which the technology can be implemented. One such example is that of a medical or healthcare practice. FIG. 1 is a diagram illustrating an example of a healthcare practice with which the disclosed technology may be implemented. In general, the healthcare practice can include one or more medical practices such as, for example, an orthopedic medicine practice, a sports medicine practice, a pediatric practice, a general practitioner/family practice, and so on. The one or more medical practices can include physicians, physician assistants, nurse practitioners, radiologists, physical therapists and other healthcare professionals. The one or more medical practices can be located in a single facility or distributed across a plurality of facilities. With reference to FIG. 1, an exemplary healthcare practice can include one or more of a server 31, server data storage 32, a front desk 33, and a billing department 34, inventory 35, treatment rooms 36, test facilities 37, scheduling and prescriptions 38, one or more healthcare providers 39, one or more surgical theaters were operating rooms 40, cloud data storage 41, and other internal resources 44 and external resources 45.

Server 31 and its associated data storage 32 can be centralized or distributed, and can be configured to store any of a number of different types of data for the healthcare practice. This can include, for example, data such as patient records, including electronic health records (EHR); scheduling information; billing information; and other information and records used in the management, operation and maintenance of the healthcare practice. In addition to data storage 32, each of the other resource units in the healthcare practice can include its own computing and data storage capabilities. In addition to or in place of data storage 32 (and other data storage capabilities) cloud storage 41 can be provided to store data and information used in the healthcare practice. Cloud store storage 41 can be configured to be accessible by server 31 as well as by other computing capabilities of the healthcare practice. Although one server 31 is illustrated, as would be apparent to one of ordinary skill in the art after reading this description, a number of different servers 31 can be provided in various logical and physical groupings.

Front desk 33 can be provided to greet and check-in patients at the healthcare facility. Depending on the size of the healthcare facility, front desk 33 may also be responsible for the functions of billing 34 and scheduling 38 as well as inventory 35. Billing 34 receives information regarding a patient visit, receives insurance and payment information from the patient, generates billing statements, records payments and tracks Accounts Receivable. The information regarding the patient visit used by billing 34 can include information such as, for example, the doctor or healthcare provider visited by the patient, supplies provided to or used in the treatment of the patient, articles delivered to the patient (e.g., a knee brace, crutches, etc.) and other information used to generate the bill. Inventory 35 can include supplies and other inventory used in the operation of the healthcare practice including inventory used in the treatment of patients. For example, in the case of an orthopedic practice, the inventory may include various elbow, knee, and other braces that may be provided or prescribed to a patient. The inventory may also include all other inventory (including consumables) used by the healthcare practice. Inventory levels can be tracked and managed electronically and the reordering of supplies can be automated. Scheduling and prescriptions 38 can be included to provide assistance with scheduling patient visits such as, for example, follow-on appointments, tests, and other events. Scheduling and prescriptions 38 can also manage patient prescriptions, which can include interfacing with pharmacies or other like fulfillment providers.

The healthcare practice generally includes one or more healthcare providers 39 to provide treatment and other services to the patients. Healthcare providers can include, for example, physicians, physician assistants, nurses, nurse practitioners, physical therapists, lab technicians and the like. The healthcare practice can also include one or more treatment rooms 36, test facilities 37 and surgical theaters 40. Treatment rooms can include, for example, locations in which a physician consults with her patient, were treatment is given to the patient. Test facilities 37 can include facilities such as x-ray facilities, MRI facilities, treadmills, ultrasound equipment, and laboratories, just to name a few.

As would be apparent to one of ordinary skill in the art after reading this description, various different healthcare practices may use other internal or external resources 44, 45 in the course of their practice. These and the other described resources can be communicatively coupled to one another, for example, using networking technology. Accordingly, electronic records and other data can be shared among the various resources to facilitate performance of a given resource's determined functions. Also, as noted above, the resources can include computing capabilities used in performance of their tasks.

As described in more detail below, client computing devices with applications running thereon can be provided for use by personnel of the various resources to manage their tasks and responsibilities. These client computing devices can be handheld computing devices (e.g., tablet computers, iPads, smart phones, laptops, etc.) and can be communicatively linked to the healthcare provider network such that information (e.g. patient information, treatment information, prescription information, billing information, and so on) can be shared between the client devices and the various resources of the healthcare practice. In example embodiments discussed below, these client devices are described as handheld computing devices. However, after reading this description, one of ordinary skill in the art will understand how to implement the features and functionality described herein using desktop, wall-mounted, equipment-integrated, or other computing devices to perform the client computing functions.

A workflow management service 48 can be included with the healthcare practice to manage the data and information in the healthcare practice and to provide information to the client computing devices. In various embodiments, workflow management service 48 can be integrated with server 31 (e.g., an application running on server 31), it can be integrated with other computing resources in the healthcare facility, or it can be a stand-alone service with dedicated computing resources. workflow management service 48 can be configured to consolidate data and information from data storage facilities within healthcare facility (e.g., cloud storage 41, data storage 32, and data stored at various resources) as well as information received from sources external to the healthcare facility.

Workflow management service 48 can be configured to gather this information and provide it to the one or more client computing devices used in the healthcare facility. For example, in some embodiments, workflow management service 48 retrieves a predefined set of information (e.g. patient electronic health records, billing records, scheduling records, etc.) and provides this information to the client computing devices. The information can be tailored for one or more client computing devices or groups of client computing devices or all of the gathered information can be sent to the client computing devices. For example, particular pieces of information relevant to a resource with which a client computing device is associated can be culled from the full set of gathered information and send to that associated client computing device. As a further example, patient health records and scheduling information may be gathered and sent to one or more client computing devices used by physicians or other healthcare providers 39 in the healthcare facility. Still further, in facilities where there are multiple healthcare workers (for example, physicians), patient records can be gathered and sorted such that each physician receives only that information pertaining to his or her patients.

As another example, billing and scheduling information might be gathered and sent to the billing department 34. Accordingly, client computing devices (or applications running thereon) can be identified with specific personnel at the healthcare facility or with particular resources or functions of the healthcare facility. In this manner, tailored sets of information can be delivered to specific client computing devices to avoid the need to download all data to all devices. In some embodiments, the client computing devices are identified by information coded into the applications. In other embodiments, the client computing devices can be identified based on login information provided by healthcare worker. In this latter example, client computing devices can be shared amongst different practitioners, such, as for example, across different shifts.

Figure 2:
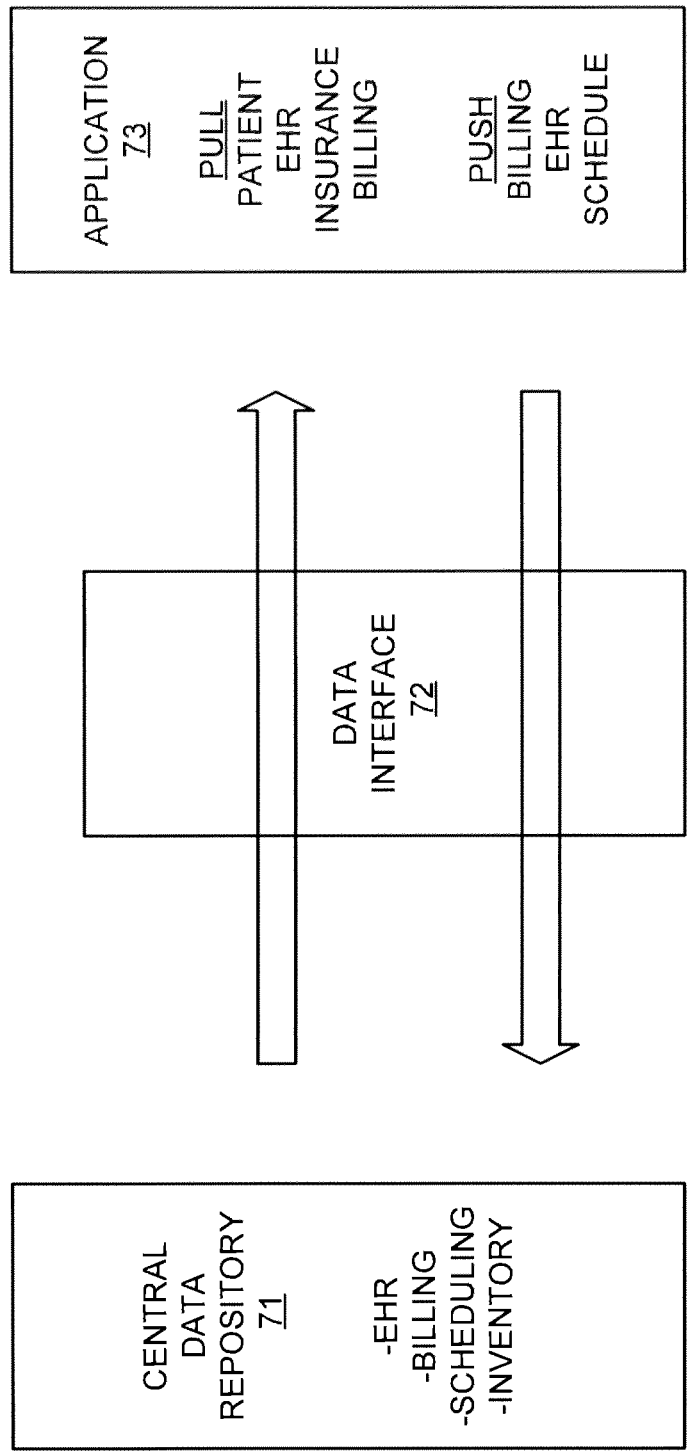
FIG. 2 is a high-level block diagram illustrating one example of information sharing in accordance with one embodiment of the technology described herein.

As stated above, in the example healthcare practice, the various resources can each include computing capabilities and various client computing devices can be provided for use as well. In order for these devices to operate well and for the functions of the healthcare practice to be integrated, these devices can be configured to share information with one another as may be relevant to their respective resource functions. FIG. 2 is a high-level block diagram illustrating one example of information sharing in accordance with one embodiment of the technology described herein. Referring now to FIG. 2, this example includes a central data repository 71, the data data interface 72, and one or more applications 73.

Central data repository 71 can be configured to store records and information germane to the healthcare practice. For example, central data repository 71 can be configured to store electronic health records (EHR), patient billing records and other billing information, patient scheduling information, resource scheduling information, inventory information, and other information relevant to the healthcare practice. Central data repository can be a centralized data store or it can encompass data storage facilities distributed within and external to the healthcare practice. For example, central data repository 71 can encompass cloud storage 41, server data storage 32, and other data storage elements. By way of example, consider a hospital environment in which a plurality of different healthcare practices may be registered to admit and treat patients in the hospital. In such an environment, central data repository 71 can comprise data storage for the hospital data records, and applications 73 from a plurality of different registered healthcare practices can be given access to the information in central data repository 71.

Application 73 can include healthcare practice management applications running on one or more client devices used in the healthcare practice. Application 73 can include the functionality to retrieve or pull information from data repository 71 including, for example, patient health records (e.g., EHR), scheduling information and billing information. Application 73 can be a single application or it can include multiple applications running on a device. As described in further detail below, application 73 can be configured to perform functions such as build a schedule for the healthcare practitioner assigned to or logged into a particular client computing device; provide patient health records and other patient information to the healthcare practitioner treating a patient; receive diagnosis and treatment information for a patient entered by a healthcare practitioner; receive prescription information for a patient from an attending physician or other healthcare practitioner; receive confirmation of delivery of prescribed materials; update inventory records based on materials prescribed and supplies used in treating a patient; update patient billing records based on information such as treatment provided, facilities and supplies utilized, materials prescribed, and the like; and receive scheduling information for future patient treatments or follow-ups.

In some embodiments, application 73 can be one or more applications configured to run on their respective client computing devices. For example, different client devices for different facility resources may run different applications 73. For example, a physician's application 73 may be provided for use by a physician on his or her client computing device. Likewise, applications 73 tailored to a physician assistant, a nurse or nurse practitioner, a laboratory or test clinician, and other facility resources can be provided. In another embodiment, application 73 can be a common application used by client computing devices at all of, or a subset of facility resources. Therefore, although the examples described herein in some instances refer to a specific application 73 (e.g., a physician's application or a nurse's application) one of ordinary skill in the art after reading this description will understand that a common application can be provided to perform functions of the specific applications. In still other embodiments, the functions of application 73 can be shared among a given client computing device and another computing resource such as, for example, workflow management 48.

Data interface 72 can be included to provide a communications interface between central data repository 71 and the one or more applications 73 used in the healthcare practice. For example, data interface 72 can be provided to retrieve the necessary particular information from central data repository 71, and provide it to one or more designated applications 73. In some embodiments, data interface 72 can be configured to pull the information from central data repository 71 and broadcast it to all client devices or applications 73, or it can selectively send certain pieces of information or certain information types to specific client devices or groups of client devices. For example, data interface 72 can be configured to send billing records and billing information to all applications 73 or client devices, or only to those application 73 or client devices used by the billing department or that may be otherwise used by personnel who would benefit by having that information.

With HIPPA in particular and other privacy concerns in general, information storage in the various data storage locations associated with and external to the healthcare practice may be encrypted or otherwise protected. Additionally, because there can be a variety of different data types accessed by the system and the data can be stored at different data storage locations, the data retrieved by data interface 72 may be in different formats. Accordingly, in some embodiments, data interface 72 can be provided with functionality to decrypt data that has been encrypted with a variety of different encryption types and encryption keys, and to re-secure the data (e.g. re-encrypt the data) prior to delivering it to applications 73. Additionally, data interface 72 can be provided with functionality to access and read data in a variety of different data formats and data types, and translate that format into one that is legible to the applications 73.

In addition to retrieving data and providing to application 73, data interface 72 can also be configured to receive data from application 73 and push or send that data to central data repository 71. This data push can be used to update healthcare records and other information at the central data repository 71 with information entered by healthcare practitioners or otherwise received from the healthcare facility in conjunction with the treatment or follow-up of the patients. For example, billing record updates, electronic health record updates, scheduling updates, prescription record updates, inventory updates, and other like information can be pushed by the applications 73 to data interface 72 (or pulled by data interface 72 from the applications 73) and provided to central data repository 71.

As with retrieval of data from central repository 71, data interface 72 can likewise ensure that the data is secure for transmission from application 73 to central repository 71, as well as perform any format changes necessary to provide the data in the proper format expected by the various components of central repository 71. For example, data sent encrypted using one encryption format by an application 73 can be decrypted by data interface 72 and re-encrypted into an encryption format anticipated by central data repository 71. Because central data depository 71 can include data stored by a number of different systems, data interface 72 can be configured to decrypt information received from one source, and re-encrypt the information for transmission to various components or systems using their respective encryption techniques.

Figure 3:
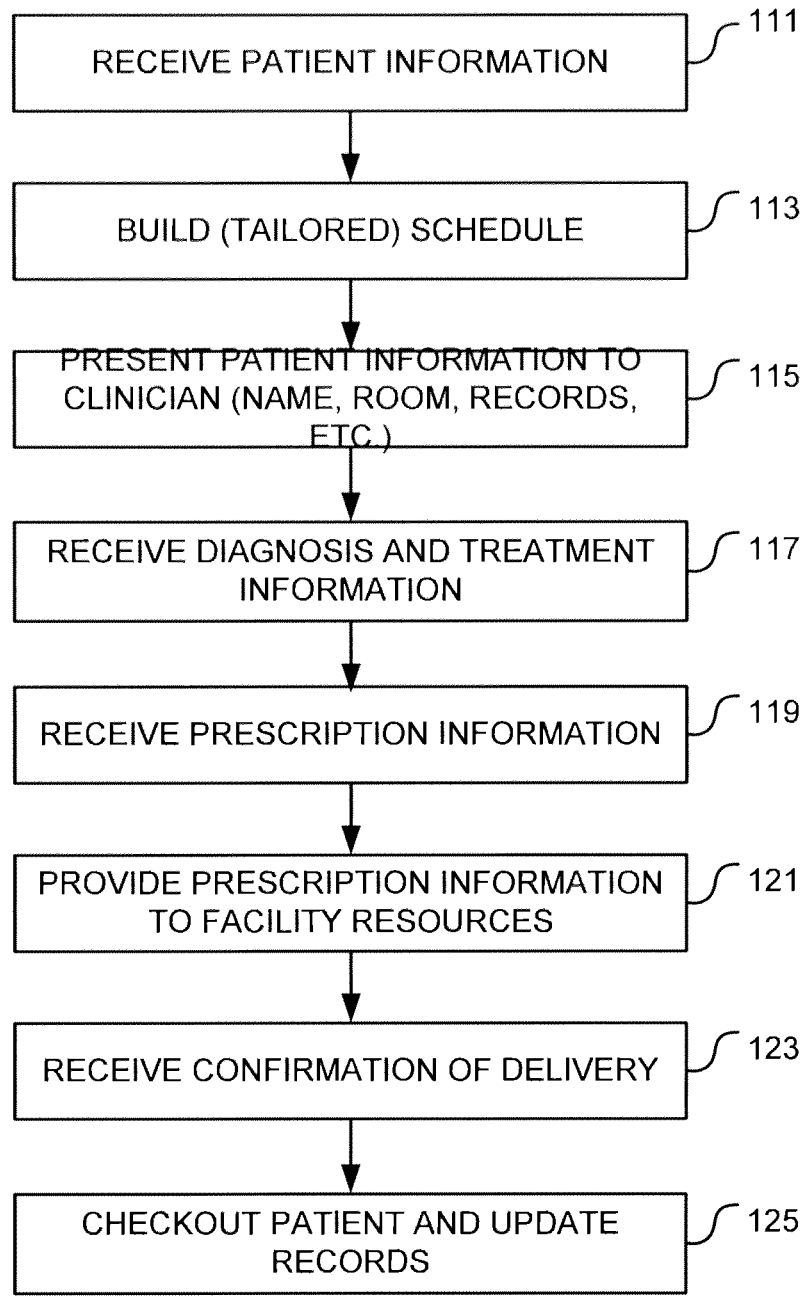
FIG. 3 is a diagram illustrating an example process that can be implemented by an application in accordance with one embodiment of the technology described herein.

FIG. 3 is a diagram illustrating an example process that can be implemented by an application 73 in accordance with one embodiment of the technology described herein. FIG. 3 provides a high-level discussion of some of the features and functionality that can be provided by one or more application 73. Various aspects of these features and functionalities are described in greater detail following the discussion of FIG. 3. Referring now to FIG. 3, at a step 111 application 73 receives patient information from data storage. For example, in terms of the embodiments described above, application 73 can receive patient information from central data storage 71 either directly or indirectly. For example, application 73 can receive data via an interface such as data interface 72. The patient information received can include health records, scheduling information, billing information and other patient-related information.

As stated above, the information received by a particular application 73 can be specific information tailored for that application. For example, a physician may log onto a client device with his or her specific ID and password. Alternatively, the application 73 may be running on a client device assigned to that particular physician. Accordingly, based on identification of the particular physician, specific patient information can be retrieved and downloaded to that application 73. In this manner, only records for patients that are identified as being seen by that physician are retrieved. In other embodiments, information for all patients can be received and the application 73 can be configured to sort and filter the information for a particular physician. For example, in one embodiment, a group of applications 73 running on different client devices may all receive information for all the patients being treated by that healthcare facility on that particular day.

At operation 113, application 73 builds a schedule of patients or activities for a particular time period (e.g., for a shift or for the day). For example, a schedule of patients and appointment times can be generated for one or more healthcare practitioners in the healthcare facility. Likewise, a schedule of patients and appointment times can be generated for facility resources such as test facilities (e.g., stress test facilities), diagnostic facilities (e.g., ultrasound equipment), treatment rooms, operating rooms, and other facility resources. Accordingly, for example, application 73 can be configured to provide a particular healthcare worker with a schedule of patients to be seen by that worker, a list of tests or treatments to be performed, and resources scheduled for those patients. As a further example application 73 can be configured to provide an ultrasound operator with a schedule of patients to be seen by the operator, a type of ultrasound procedure to be performed for each patient, and particular ultrasound equipment (if any) to be used for the procedure for each patient.

Application 73 can be configured to sort the schedule based on attending physician, designated treatment room, and the like. Accordingly, when the healthcare provider accesses the application 73, the healthcare provider can access the schedule of patients assigned to his or her rounds for that day. Because the application 73 received information for all patients (or a group of patients) the healthcare provider can also have access to schedules and other information for patients being seen by other practitioners.

At operation 115, application 73 displays schedule information to the healthcare worker. For example, application 73 can be configured to present a list of scheduled appointment times and patient names to the healthcare worker. As noted above, the information can be filtered for the particular healthcare worker or resource associated with the application 73. Alternatively, the information can include scheduled appointment times and patient names for other patients as well. In such embodiments, application 73 can be configured to sort the information based on a plurality of different sort criteria.

The schedule includes buttons, links or other UI keys allowing the healthcare worker to select a particular patient or appointment and retrieve additional information about that patient or appointment. Selection of a particular patient or appointment can allow the healthcare worker to access information such as patient health records, billing information, purpose of visit, and so on. Accordingly, the healthcare worker can access information about the patient in order to provide the intended treatment. Upon providing the treatment, the application allows the healthcare worker to enter information about the treatment. This is illustrated by operation 117 in which the application receives a diagnosis and treatment information entered by the healthcare worker.

In some cases, the diagnosis or treatment of the patient will lead to a prescription for that patient. The prescription can be for medications, or for devices (e.g., crutches, knee or elbow brace, eyeglasses, etc.). Likewise, the physician may prescribe follow-on treatments, exercise regimens, dietary restrictions, or other procedures or activities. On determining whether one or more prescriptions are appropriate for the patient, the healthcare provider can enter the prescription information into the client computing device. For example, in one embodiment, upon the entry of diagnosis and treatment information, application 73 can prompt the healthcare provider to enter prescription information. At operation 119, application 73 receives the prescription information and stores it as part of patient's updated health records. The prescription information can be shared with other resources at the healthcare facility for fulfillment of the prescription. Accordingly, at operation 121 the prescription information is provided to the appropriate resources at the healthcare facility. For example, in the case of a prescription for medicaments, the prescription record can be provided to the front desk and a written prescription given to the patient upon checkout. Likewise, the prescription can be electronically transmitted to a pharmacy and the patient provided with a confirmation on checkout regarding the prescription and the pharmacy. As yet another example, the prescription can be electronically transmitted to an on-site pharmacy an on-site pharmacy such that it can be fulfilled and the prescription can be picked up by the patient before departing the facility, or can be picked up by a healthcare worker and delivered to the patient.

As another example, consider a case in which the prescription is for an orthopedic apparatus such as an elbow or knee brace. This usually involves fitting the apparatus to the patient. In this example, the prescription can be delivered to a nurse practitioner or physician assistant who is designated to fit the device to the patient. In various embodiments, the nurse practitioner or physician assistant also uses a client computing device to receive the prescription information and to fulfill the prescription. Particularly, the healthcare worker is notified via application 73 on his or her client computing device that an orthopedic apparatus has been prescribed for patient and that the patient is ready for fitting. In other embodiments, paper or other records can be used to notify the health care worker that the orthopedic apparatus has been prescribed for patient. The information provided to the physician assistant can include an identification of the orthopedic apparatus to be provided and any fitting instructions necessary. Accordingly, the physician assistant retrieves the prescribed orthopedic apparatus from inventory and fits the apparatus onto the patient. Once the orthopedic apparatus is fitted, the physician assistant can update the client computing device with confirmation of the fitment. Accordingly, at operation 123, application 73 receives confirmation of delivery of the prescribed orthopedic apparatus.

When the treatment is completed, the healthcare worker can indicate such completion in a window of application 73, and application 73 can begin checking out the patient. This is illustrated by operation 125. As part of the checkout process, patient records can be updated and instructions can be given to workers at the healthcare facility to facilitate the checkout process. For example, diagnosis information, prescription information, test results, follow-up instructions, and other information relating to the patient's visit is gathered by application 73 during the patient's visit. This information can be uploaded to central data repository 71 (e.g., via data interface 72) to update patient records.

Uploads to a central data repository 71 for this and other data types can be performed in real-time or near-real-time during the patient visit, upon completion of the patient visit, or in a batch mode at predetermined time intervals (e.g., at the close of business). Billing information can be compiled for the patient visit, tests performed, supplies provided, prescription items delivered in other billing information. Likewise, payment information can be compiled for the patient including payments or copayments made by the patient, insurance information, and receives insurance endorsements. This information can also be provided to central data repository 71. Additionally, where follow-up visits or future tests are scheduled, the scheduling information can be accepted by application 73 and also uploaded to central data repository 71.

Figure 4:
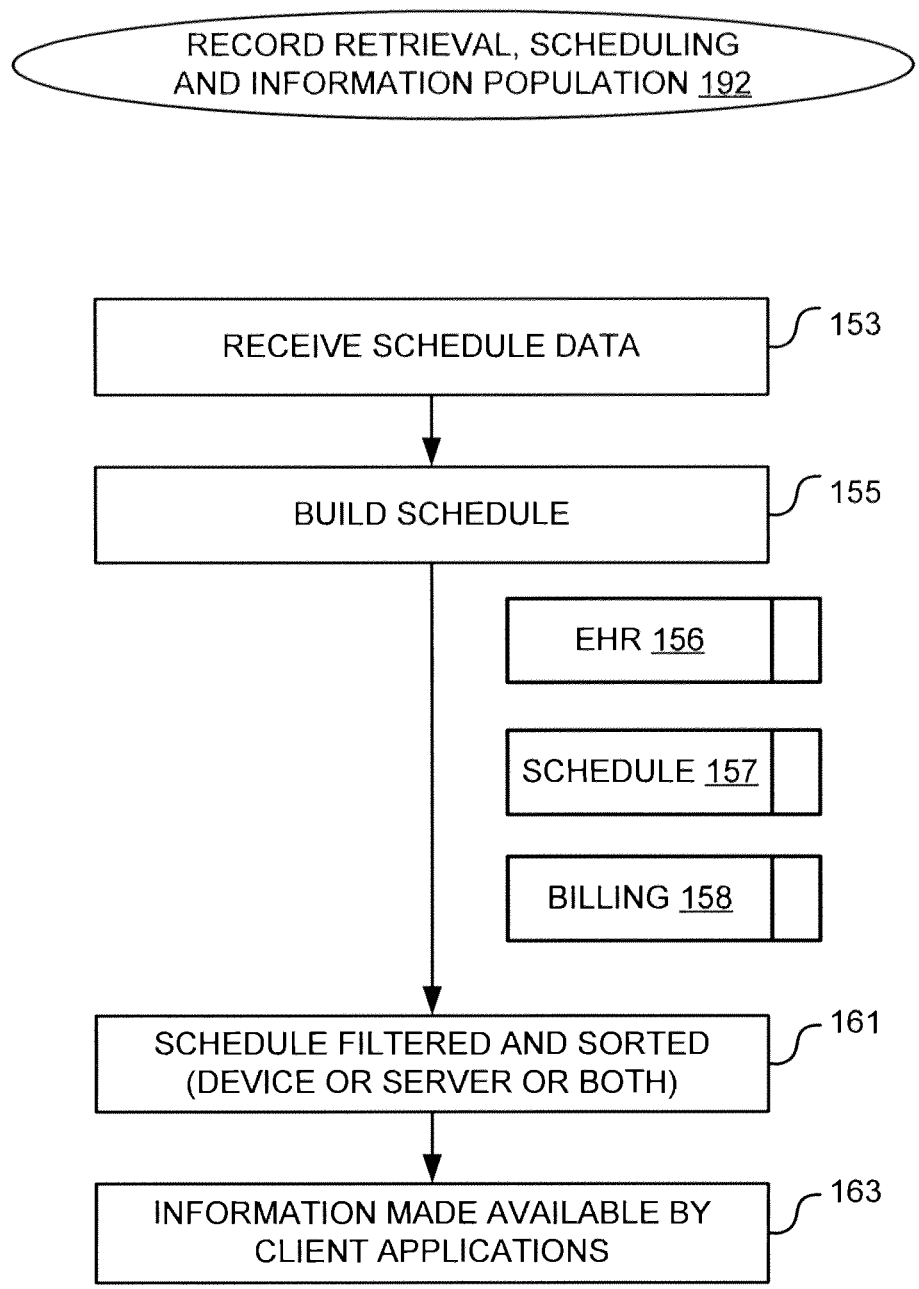
FIG. 4 is an operational flow diagram illustrating an example process for scheduling in accordance with one embodiment of the technology described herein.

FIG. 4 is an operational flow diagram illustrating an example process for scheduling in accordance with one embodiment of the technology described herein. Referring now to FIG. 4, at operation 153, application 73 receives schedule data. For example, application 73 can be configured to pull information from central data repository 71. Information pulled can include information such as patient information and schedule information. Additionally, at this step application 73 can pull all information for patient visits (even if it is not used for scheduling) during the pull operation.

At operation 155, application 73 builds a schedule. The schedule can be a master schedule for the healthcare facility, individual schedules for healthcare facility resources (e.g. physicians, test equipment, treatment rooms, etc.) or both. Accordingly, the schedule can be built by an individual application 73 running on a particular client computing device, or it can be built by a centralized application (e.g., an application 73 running as part of workflow management 48). In some embodiments, the schedule can be a scheduled listing of patients to be seen at the healthcare facility and the schedule times of their appointments. The schedule can be generated so as to display on the client computing devices for review or approval by healthcare practitioners.

At operation 161 the schedule can be filtered or sorted, or both, for a particular application 73 or group of applications 73. For example, where multiple physicians hold hours in the healthcare facility, the schedule can be filtered or sorted by physician (or by other caregiver). Therefore, a physician only needs to view his or her schedule patients when planning the day or conducting rounds. As another example, the schedule can be sorted or filtered based on test facilities or equipment, treatment rooms, operating rooms, or other resource designation. This can allow a caregiver responsible for operating a particular facility or resource to view a schedule tailored to the resources for which he or she is responsible. In some embodiments, an application might only request the information that is relevant to the resource with which it is associated, thereby building a tailored schedule for that application. In other embodiments, a master application (whether on a client device, part of workflow management 48, or otherwise) can build one or more schedules for a plurality of applications 73 and deliver those schedules (filtered, sorted, or otherwise) to the appropriate applications 73. In yet another embodiment, the schedule or schedules can be built by computing resources at central data repository 71 and distributed to the client resources.

At operation 163, patient records are made available by the client applications 73 to the healthcare provider. The patient records can include information such as, for example, electronic health records (EHR) 156 of the patient, scheduling information 157 of the patient and patient billing records 158. The patient records may also include outcome-related data and information, including information relating to recovery of the patient. For example, this can include the patient's post-surgery recovery status, response to physical therapy or other follow-on treatments, success of a fitted brace, and so on. The electronic health records 156 can include information from past visits by the patient as well as electronic health records for that patient transferred to the healthcare facility by a previous caregiver. Accordingly, by opening a schedule entry, that that patient's healthcare records can be reviewed by the healthcare provider before, during and after the patient visit. Electronic health records may for example, contain information pertaining to a patient's condition, results of prior tests, prior diagnoses, x-rays, prior prescriptions, prescribed medications, follow-up information, and other information normally found in a patient's health records. Electronic health records can be updated by the caregiver during treatment.

Schedule information 157 can include information regarding a scheduled time and place for the current appointment and any other scheduling information that may be relevant. Billing information 158 can include information about a patient's account history including, for example, insurance information, prior payment information, account balances, and so on. Insurance information may be useful, for example, to inform the caregiver as to what treatment options may be available depending on a patient's coverage. While billing information might not be important to a physician for purposes of the office visit, this information can be accessed by other resources including the front desk, which may need to collect co-pays or additional insurance information, or the billing department, which may need to update its records and send out billing or reminder statements.

Accordingly, clicking on or otherwise opening a schedule entry can provide the healthcare practitioner with access to patient information 156, 157, 158 about the patient corresponding to that entry and his or her treatment.

Figure 5:
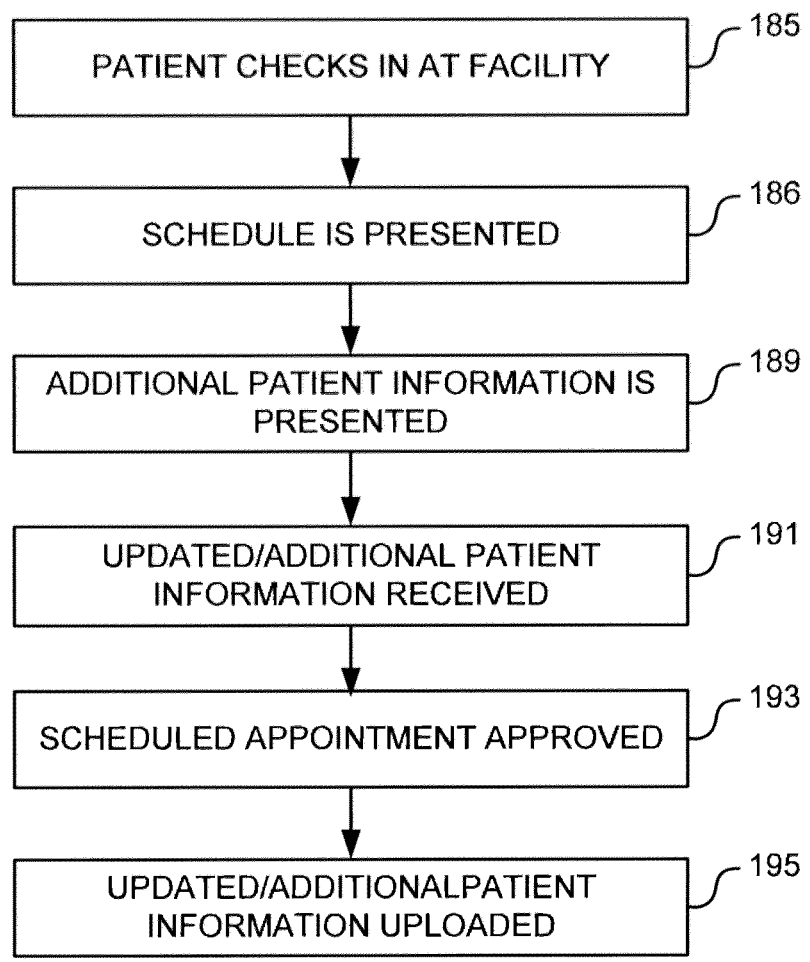
FIG. 5 is an operational flow diagram illustrating an example process performed by an application to facilitate patient check-in to the healthcare facility.

FIG. 5 is an operational flow diagram illustrating an example process performed by an application to facilitate patient check-in to the healthcare facility. At operation 185 a patient arrives at and checks in to the healthcare facility. For example, the patient may sign in at a front desk and provide the front desk attendant with his or her name or identification. As another example, a kiosk may be provided to allow self check-in. Application 73 provides the schedule to the front desk attendant at operation 186. For example, the schedule can be displayed on a display screen of a client computing device for the front desk. The attendant can consult the schedule to locate the patient checking in.

The reception-desk attendant can open the appropriate schedule entry to view additional patient information that may be pertinent to the check-in process. At operation 189 this information is presented to the attendant. This information can include, for example, information such as a paperwork that will need to be prepared by the patient prior to the appointment, insurance information that may be required from the patient, and other information. If additional information is required from the patient, this information can be requested of an obtained from the patient. The attendant can enter the updated information into the application. For example, the attendant can enter new or updated insurance information, and indication that appropriate copayments were made, and so on. This information is received by the application to update patient records. This is indicated by operation 191.

When the information is completed, at operation 193 the scheduled appointment is approved so the patient can be seen. In some embodiments, requiring approval of the appointment at one or more steps along the appointment process can serve as a gatekeeping function to manage patient flow. For example, the schedule may be locked or flagged for certain resource applications until approval at or prior gatekeeping step is given. As a further example, the schedule appearing on a physician's application may be marked with a flag, highlighted, or otherwise noted as being locked until approval by the front desk is provided. As yet a further example, the schedule appearing on a test operator's application may be locked until the physician has seen the patient and approved the patient's condition for the test.

Operation 195 any updated or additional information obtained from the patient during the check-in process can be stored locally by the client computing device, and uploaded to central data repository 71 to update the main record database. This upload to central data repository 71 can be done in real time or near real-time, or can be done in a batch mode at periodic (e.g. daily) intervals.

Figure 6:
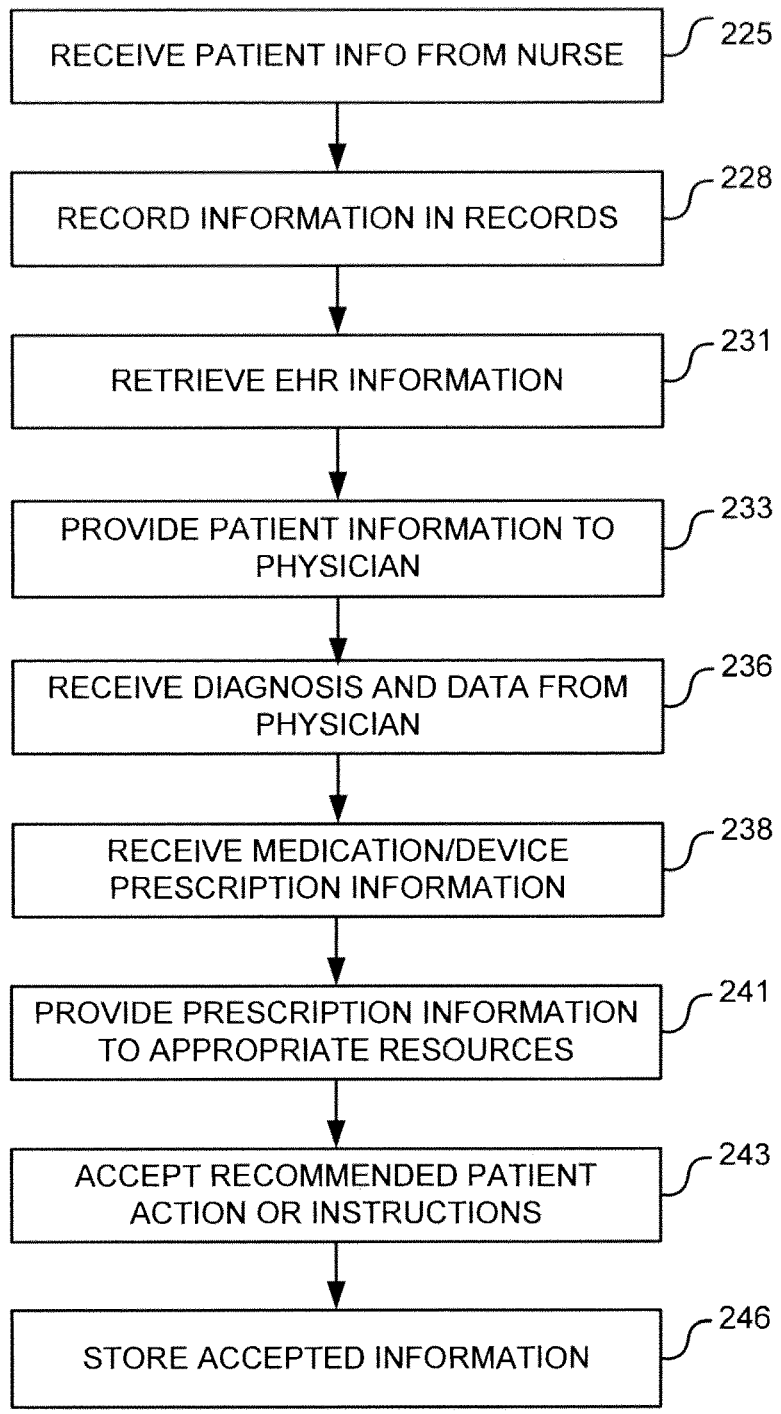
FIG. 6 is an operational flow diagram illustrating an example process for providing data to and accepting data from one or more healthcare practitioners who may be examining or treating the patient.

As described above, in various embodiments one or more application 73 can be used to provide patient data to and accept patient data from one or more healthcare practitioners. FIG. 6 is an operational flow diagram illustrating an example process for providing data to and accepting data from one or more healthcare practitioners who may be examining or treating the patient. For clarity and ease of discussion, FIG. 6 is described in terms of the specific example. The specific example is that of the patient who is first seen by a nurse and then by a physician. In this example, the nurse performs preliminary blood pressure, heart rate, temperature, and weight measurements on the patient. Subsequent to these measurements, the physician examines the patient. While the example shown in FIG. 6 is an example use of the application by a nurse and a physician during a patient visit, one of ordinary skill in the art after reading this description will appreciate how the application can be configured to operate with other healthcare resources or practitioners.

Referring now to FIG. 6, at operation to 225 the application is configured to receive patient information from the nurse. For example, in operation when a nurse calls a patient into for examination, the nurse can open the patient schedule using the application on his or her client computing device and enter a data entry mode. The nurse can then make the desired patient measurements (e.g., weight, blood pressure, pulse, etc.) and enter the results into the client computing device. These results are received by the application and the application updates the patient's health records accordingly. This is illustrated by operation 228. In the above-described example, manual entry of the results are accepted by the client computing device. In other embodiments, wireless, hardwired or other electronic communication can be provided between the measurement equipment (e.g., scale, sphygmomanometer, etc.) and the data transferred electronically.

At operation 231, the physician application retrieves electronic health records. In some embodiments, this information can be downloaded when the schedules are created and stored locally to the client computing device for access by the application when needed. In other embodiments, information can be downloaded when the patient is check-in or at the start of the patient's appointment.

At operation 233, the patient's health records are made available to the physician. For example, in one embodiment, a button or other icon can be provided on the user interface such static physician can click to access the health records. Upon accessing health records, it can be displayed by the application to the physician on the user interface of the client computing device. This is done so that the physician attending to the patient can review the patient's records prior to and during the treatment. Where multiple pages of health records are involved, the user interface can allow a position to scroll through health records and patient history to obtain information needed. Additionally, search functions can be provided to locate specific items of information within the health records. Although not illustrated in FIG. 6, the nurse's application can also retrieve and display electronic health records of the patient.

At operation 236, the physician's application accepts treatment information from the physician. This treatment information can include information such as, for example, the diagnosis and information about the diagnosis, information obtained by the physician during treatment, physician observations, and other information the physician may deem useful, important or required for the health records. Particularly, the physician examines the patient and gathers information about the patient's condition. The physician may make a diagnosis regarding the patient's condition as well. The physician's application provides a window or data entry screen into which the physician can enter this data. Accordingly, the application can update the patient's health records with the current diagnosis, treatment information, recommendations by the physician, and other information entered by the position. The data entry can be made using a keyboard (touchscreen or otherwise), speech recognition software, or other data entry techniques.

During the course of the patient visit, the physician may also prescribe or recommend medication, treatment devices (e.g., an orthopedic apparatus, crutches, etc.), tests, and so on. Accordingly, at operation 238 the physician's application user interface provides a window or screen into which this information can be entered. Upon entry, the application receives the entered information, creates an order record for the prescribed item(s), and updates the health records of the patient. The order record can include, for example, identification of the prescribed item, prescription instructions, and other prescription information. The identification of the prescribed item can include, for example, a medication and unit dosage; an identification of a specific apparatus like a particular knee or elbow brace; identification of follow-up tests or procedures and so on. The prescription instructions can include, for example, patient dosages for medication and other information relevant to the prescribed item.

In some embodiments, the physician may be required to enter a PIN or other authorization code before the prescription is accepted by the system. This can add a measure of security to the system, allowing only authorized personnel to enter prescriptions or certain orders. This can also be used to track inventory to a particular practice or physician. In some embodiments, the physician's original login is sufficient authorization for entry of the prescription. In other embodiments, a separate PIN or authorization code is required. Additionally, in some embodiments, the prescription information is provided to other healthcare facility resources for follow-on action. This is illustrated by operation 241. In various embodiments, particular resources can be identified to receive prescription information for particular prescriptions or orders. For example, the prescription may be sent to a particular resource based on the prescription type. That is, prescriptions for medications can be sent to the front desk for printing or to an in-house pharmacy; while prescriptions for orthopedic devices may be sent to a physician assistant who can retrieve the prescribed apparatus from storage and properly fit the apparatus to the patient. An example of this is described in greater detail below.

In addition to prescriptions described above, the physician may provide instructions or other information to the patient regarding future courses of action. For example, the physician may recommend a particular diet or exercise routine to the patient. Additionally, the physician may recommend or follow-up tests or procedures for the patient. Accordingly, at operation 243, the physician's application is configured to accept these recommended patient actions or instructions. For example, the physician's application may provide a data entry window or screen allowing the physician to enter this information.

At operation 246, the information entered at operations 236, 238, and 241 can be used to update the patient health records at central data repository 241. As with other data updates the can be provided using the technology disclosed herein, this data update can be made in real-time or near-real-time as the data is entered, or it can be uploaded to central data storage 71 at a predetermined time or at predetermined time intervals (e.g. at the end of a shift, at the close of business, or other designated time).

Figure 7:
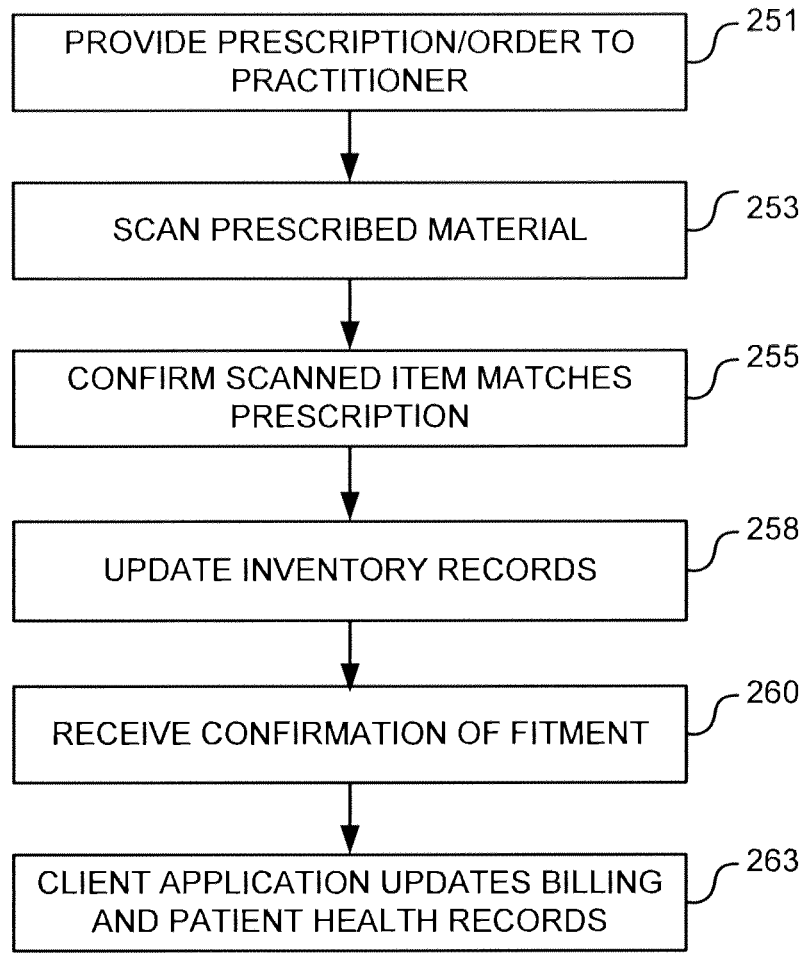
FIG. 7 is an operational flow diagram illustrating an example process for managing the delivery of a prescribed item in accordance with one embodiment of the technology described herein.

FIG. 7 is an operational flow diagram illustrating an example process for managing the delivery of a prescribed item in accordance with one embodiment of the technology described herein. As discussed above, in various embodiments, the application 73 (e.g. a physician's application) can accept and receive prescription information for a patient. This prescription can be entered by the physician or other prescribing clinician at the appropriate user interface of the application 73. For clarity and ease of description, the process of FIG. 7 is described in terms of a specific example in which a patient is prescribed a particular knee brace. After reading this description, it will become apparent to one of ordinary skill in the art how this process can be applied for other prescriptions or orders.

Referring now to FIG. 7, at operation 251, prescription or order is provided to the physician assistant who is going to fit the knee brace on to the patient. Particularly, in some embodiments, the physician's application can be configured to send the prescription to the physician assistant's application. Accordingly, the physician assistant can view the prescription on his or her client computing device, determine the prescribed knee brace, and retrieve it from inventory. A key code can be provided with the prescription to allow the physician assistant access to the inventory.

At operation 253, the prescribed item scanned by the physician assistant's application. For example, the application can include recognition software configured to recognize a barcode, stock number, RFID tag, NFC tag, or other like identification of an item retrieved by the physician assistant from inventory. The identification of the item retrieved compared to the item identified in the prescription information to determine whether the correct item has been pulled from inventory. Accordingly at operation 255, the physician assistant's application confirms that the scanned item matches the prescription. Once confirmed, the inventory records can be updated to reflect the fact that the item has been removed from inventory. This is shown at operation 258.

With the prescribed item in hand, the physician assistant can return to the treatment room to fit the knee brace to the patient. The physician assistant can instruct the patient on proper fitting, application and adjustment of the knee brace, as well as provide patient any other information here she may need regarding the product. The application allows the physician assistant to confirm that the prescribed item was in fact delivered to the patient. Accordingly, at operation 260, the physician assistant's application receives confirmation of the delivery. As is the case with the physician's application described above, the physician assistant's application can be configured to accept diagnosis, treatment, and other information from the physician assistant, and it can allow the physician assistant to identify or recommend exercises, follow-up tests, or other follow-on opportunities for the patient. At operation 263, information provided by the physician assistant can be used to update the patient's billing and health records.

If the item prescribed to the patient does not fit properly or is otherwise not delivered to the patient, the item may be returned to inventory or discarded. In the event an item is returned to inventory, the physician assistant can note the return through his or her application, and the application can update the inventory records accordingly.

Figure 8:
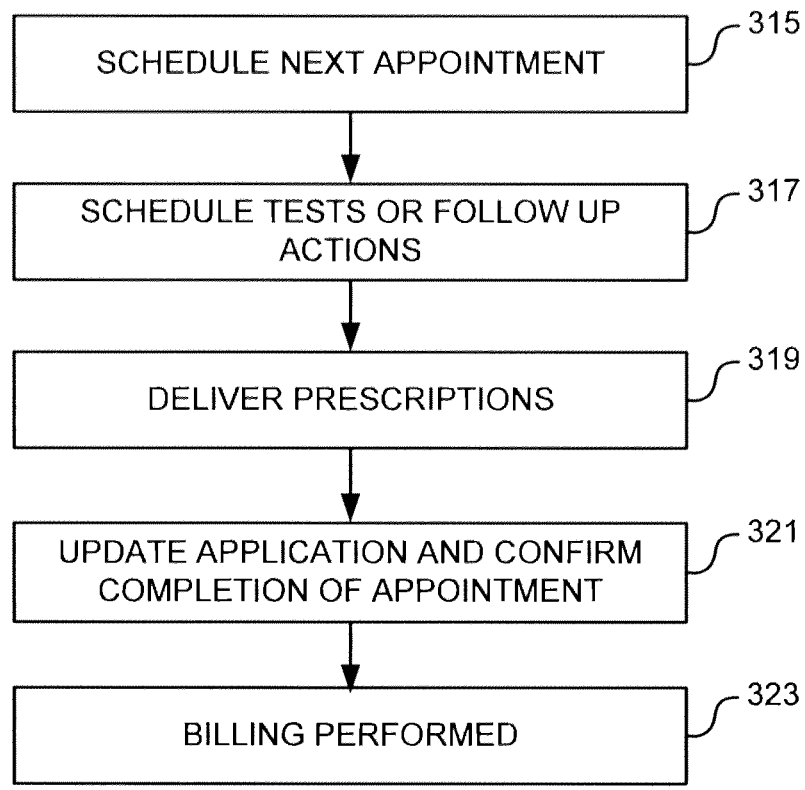
FIG. 8 is an operational flow diagram illustrating an example process for patient check out in accordance with one embodiment of the technology described herein.

With the patient having been examined by a physician and having received any prescribed deliverable items, the patient may now begin the checkout process from the facility. An example process for checking out the patient is illustrated in FIG. 8 in accordance with one embodiment of the technology described herein. The checkout process can entail scheduling a next appointment, and scheduling tests or other follow-up actions. Accordingly, at operations 315 and 317, the front desk application can allow the attendant to schedule the next appoint and any follow up tests or actions.

At operation 319, the attendant can deliver prescriptions to the patient. For example, where the practitioner prescribed medication for the patient and prescription for that medication into the application, that prescription can be delivered to the front desk application. The attendant can retrieve the prescription and print it out for the patient. Additionally, instructions and other materials identified by the healthcare practitioner can be printed and delivered to the patient at this time. Alternatively, diet routines, exercise regimens and other materials can be provided to fax, e-mail or otherwise transmit the prescription to a patient's desired pharmacy. In some embodiments videos or other multimedia content can be stored on the system and prescribed to the patient. For example, follow-on care instructions, specific exercise routines, safety information and other information and materials may be stored on the system and prescribed to the patient for viewing. Accordingly, the system can be configured to email or otherwise deliver the content, or links to the content, to the patient for access. Authentication or login codes may also be provided to the patient for such access.

At operation 321, the attendant can update the patient's information with any additional information and confirm completion of the appointment. This information can be received by the attendant's application and made available for printout. Alternatively, it can be e-mailed to the patient had a designated e-mail address.

At operation 323, the billing information can be collected in the appropriate bill assembled for the patient. This can be done by a billing application within a billing department 34 or at front desk 33 (or other location as determined for a particular facility). Billing records can be updated to include the visit and any pertinent details regarding the visit, materials and supplies used for the visit or provided to the patient, tests or other operations performed, and so on.

As the above examples illustrate, various embodiments of the application 73 provide the opportunity for a physician, practitioner, clinician, or other healthcare worker to enter information pertaining to a patient visit into the client computing device. In various embodiments, depending on the type of information, application 73 may prompt the user to enter particular types of information. In other embodiments, healthcare worker may be required to initiate the data entry process. Various forms of data entry can be provided including, for example, keyboard entry, touchscreen entry, voice-recognition, menu selections, and the like.

For example, a menu of selections can be provided to allow the user to select particular data entry items. As a further example, where the physician intends to prescribe a knee brace, the application provide on the UI a menu of available knee braces, allowing the physician to select from among the list of possibilities. As yet another example, the physician may call up a list of different diet regimens and select one or more diet regimens for among those listed to be prescribed to and delivered to the patient. These can be provided as pre-written instructions or pre-prepared diets to be selected for entry into the patient's health records and for delivery to the patient. Similarly, a listing of tests or other follow-on procedures can be provided from which the physician can choose.

As stated above with reference to FIG. 2, in various embodiments a data interface 72 can be provided to transfer data between central data repository 71 and one or more applications 73. Embodiments of the invention can be implemented to provide the transfer in a manner that is compliant with the security and privacy requirements of the Health Insurance Portability and Accountability Act of 1996

(HIPAA). Additionally, embodiments can be implemented to allow secure sharing (including HIPAA-compliancy) of patient electronic health records (EHR) among doctors, hospitals and other healthcare workers and facilities.

Embodiments of the invention can be configured to allow a patient to visit a healthcare facility and allow that healthcare facility to electronically and securely access that patient's healthcare records from a remote location (or from local servers) for use in examining or treating the patient. In some embodiments as more fully described below, patient health records can be flagged for delivery at a data repository and made available for transfer. A transfer utility can be configured to access the files, encrypt the data (original encryption, or second- or $n^{th}$-layer encryption) and transfer them to the physician or his/her practice. A portal can be provided to receive the data from the transfer utility and manage delivery to the designated physician/practice. For example, the portal can be configured to queue the items for delivery, add another layer of encryption, send the items to the practice/physician, check for and store pending successful delivery. The data file or packet received from the repository can include routing information such as the data source (i.e., which repository sent the data) and the destination (e.g., the physician or practice to which the file or packet is to be sent).

The physician or his/her practice (or other healthcare worker or healthcare facility) can include one or more client devices to receive the files sent from the portal. The client devices (e.g., handheld, desktop or other computing device) can be configured to receive the data, decrypt the data (each layer if multiple layers), perform any necessary data conversion (e.g., from the data type used at the data repository to a data type recognized by one or more applications used by the physician or facility) and deliver the data to the appropriate application(s). The data received (or pulled) from the central repository can include patient information, billing information, EHR data, etc. The client devices (e.g., applications running thereon) can use this data to build a schedule (e.g., schedule of patient visits), link data to the schedule (e.g., link a patient's records, X-Rays, etc. to his/her corresponding schedule entry), update billing and payment records and the like. The client devices (e.g., applications running thereon) can allow the physician to enter information about the visit, can allow billing information to be updated, can allow inventory information to be updated, and the like. Updated information can be sent back to the data repository either through the portal (e.g., in a process as described above) or otherwise.

Figure 9:
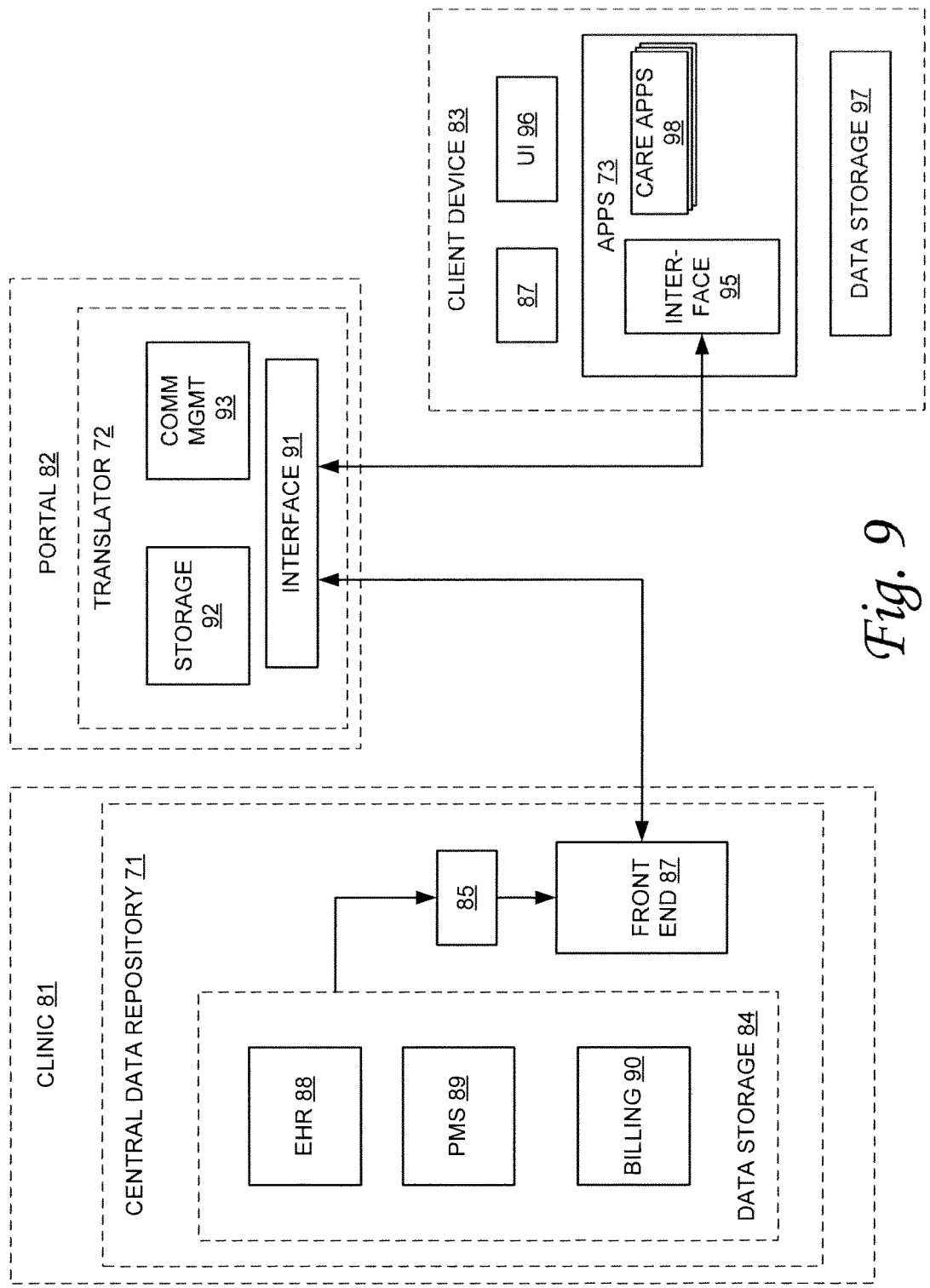
FIG. 9 is a block diagram illustrating an example data management system in accordance with one embodiment of the technology described herein

FIG. 9 is a diagram illustrating an example block diagram for a data management system and healthcare-practice management system in accordance with one embodiment of the technology described herein. Referring now to FIG. 9, the illustrated example data management system includes a clinic 81, a portal 82, and a client device 83. Although each of these items is illustrated as a single entity, one or more of any of these items can be provided in a given application as may be desired. For example, there can be multiple client devices 83 interfacing through a portal to one or more central data repositories 81. In various embodiments, and in the illustrated example, central data repository 81, portal 82, and client device 83 can be implemented to provide the same features and functionality as described above with reference to FIGS. 2-8. Particularly, FIG. 9 provides one example implementation of the healthcare management system in which clinic 81 includes a central data repository 71, portal 82 includes a translator 72, and client device 83 includes one or more applications 73. FIG. 9 and its accompanying description provides more information on the data transfer and storage aspects of such a healthcare management system.

With continued reference to FIG. 9, clinic 81 in this example includes a central data repository 71. In the illustrated example, central data repository 71 includes data storage 84, transfer storage 85, and a communications front end 87.

In the illustrated example, data storage 84 includes the storage of various health or health-related, or patient-related, records such as patient electronic healthcare records 88, patient management system records 89, and patient billing system records 90. Each of these records can be stored in one or more data storage devices or facilities used by or having access to central data repository 71. For example, clinic 81 can include one or more computerized systems to allow entry, maintenance, updating and storage of the records stored in these databases. For example, a patient management system can be provided in the clinic to manage information such as patient personal information (e.g. name, address, Social Security number, etc.), patient scheduling information (e.g. times and dates of previous and future appointments), patient-attending-physician information, and so on. Such a patient management system stores its information in patient management system records 89. As another example, a billing system can be provided to manage a patient's billing information. The system can allow entry, tracking, maintenance and updating of patient billing information such as, for example, patient insurance information, billing address, payment information, payment history, Accounts Receivable, and the like. Such a billing system can be configured to store its information and billing information data store 90.

Temporary data storage 85 can also be provided to facilitate transfer of information to client devices 83. The operation of temporary data storage 85 in accordance with one or more embodiments is described in further detail below with reference to FIG. 10. Front end 87 can also be provided to provide a communications interface to other entities in the system. For example, in the illustrated embodiment, front end 87 provide significations interface to portal 82. Front end 87 can provide two-way communications, including two-way communications to an interface 91 at portal 82. In various embodiments, front end 87 can provide any necessary format conversion as may be necessary or desired to allow a seamless transfer of information among the entities. Likewise, front end 87 can also provide data encryption to add a measure of security to the data transfer. Data can be encrypted according to various standards or other encryption techniques depending on the level of security required or desired. For example, in one embodiment, military grade encryption is provided.

Portal 82 can be configured to provide temporary or long term data storage for data being transferred among the various entities. Portal 82 can also be configured to provide any additional encryption as may be necessary or desired to further secure information be transferred among the entities. Similarly, portal 82 can be configured to decrypt and re-encrypt information to provide compatibility of encryption standards or encryption keys among entities which may otherwise be incompatible in that regard. Portal 82 can also be configured to track the transmission and receipt of information sent through it, by it, or to it, to confirm proper and complete receipt of information by itself or the intended recipient or recipients. In the illustrated example, portal 82 includes a translator 72. Translator 72 includes data storage 92, communications management 93 and a communications interface 91. Storage 92 can be included to provide temporary or longer-term data storage for files, packets, records, or other information received by portal 82. For example, storage 92 can be configured to store data packets received from one entity and sent to another until such time as confirmation of receipt is received from the recipient. Interface 91 can be included to provide a communications interface between portal 82 and the other entities. For example, interface 91 can provide the physical layer functions for medications by portal 82. Additionally, interface 91 can be configured to provide any encryption or decryption that may be used, format conversion, and other communications functions. Communications management module 93 may be included to provide management and oversight of interface 91.

Is illustrated in FIG. 9, a client device 83 is also provided. In particular, one or more client devices can be provided for use by physicians or other healthcare practitioners or healthcare workers had a medical office or healthcare practice, or at another type of healthcare facility. In the illustrated example, client device 83 includes one or more applications 73. Applications 73 can include one or more healthcare management applications 98 and an interface application 95. For example, the features and functionality described above with reference to the various embodiments can be implemented using one or more application 73 on one or more client devices 83. Although one or more separate healthcare management applications 98 and interface application 95 are shown, as would be appreciated by one of ordinary skill in the art after reading this description, lease can be implemented as a single consolidated application 73.

Interface 95 can be included to provide interface functions to allow transfer of data to and from the other entities in the system. For example, interface application 95 can be provided at to manage communications between client device 83 and portal 82. Particularly, in some embodiments, interface application 95 can provide encryption, decryption, data translation or format conversion, data transfer management, and other functions useful in or desirable for the transfer of information between client device 83 and the other entities.

Client device 83 can also include data storage 97 to store data, records, and other information used by application 73. Additionally, client device 83 may also include temporary data storage 85 that may be used by client device 83 and interface application 95 to facilitate receipt and transfer of information between client device 83 and the other entities.

Also illustrated, is a user interface 96 they can be provided to allow applications 73 to interface with users of the applications. For example, in one embodiment, (e.g., such as a handheld computing device embodiment) user interface 96 can be a touchscreen interface allowing the display of information to the user as well as capturing input provided by the user. As will be apparent to one of ordinary skill in the art after reading this description any of a number of different types of user interfaces can be provided.

Although not specifically described above or illustrated in the drawing, the elements and modules described above with reference to FIG. 9 can include processing modules and other computing resources used to implement the features and functionality described herein. For example, one of ordinary skill in the art after reading this description, will understand how one or more computing systems (e.g. enterprise computing systems, desktop computing systems, workstations, computing modules such as described below with reference to FIG. 11, and other computing resources) can be used to perform features and functionality described herein.

Figure 10:
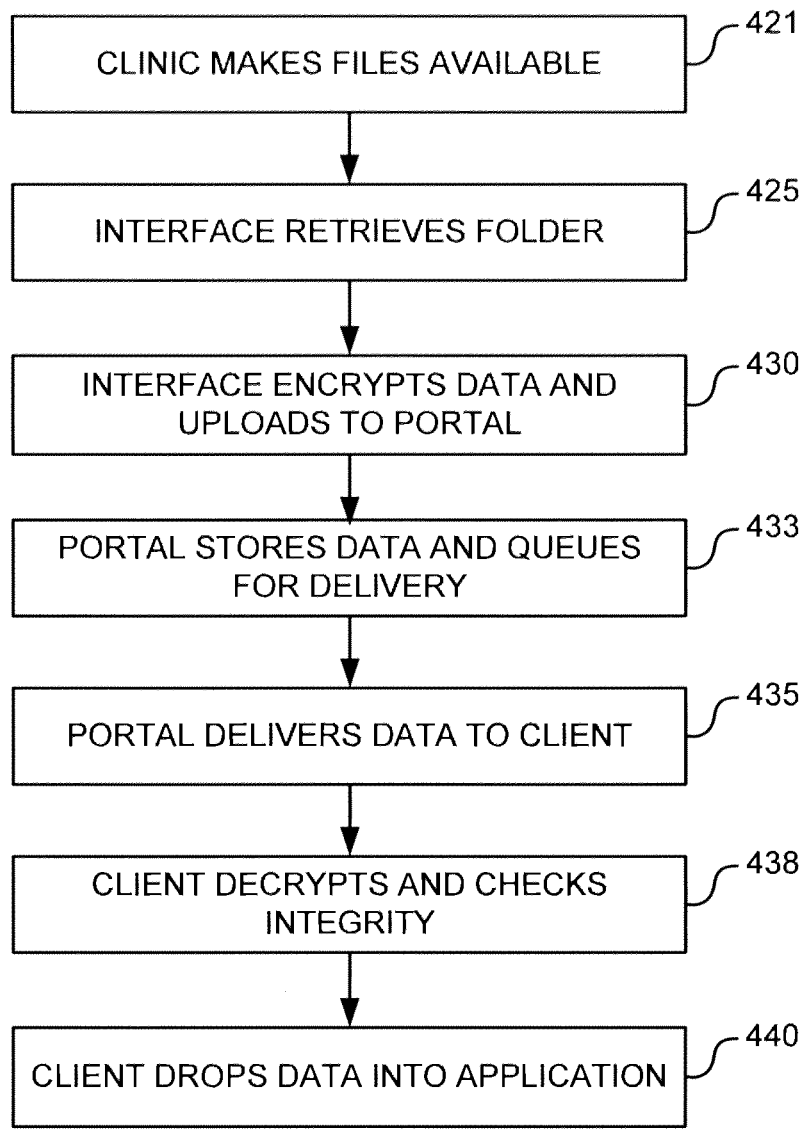
FIG. 10 is an operational flow diagram illustrating an example process for transferring information used by a healthcare management system in accordance with one embodiment of the technology described herein.

FIG. 10 is a block diagram illustrating an example process by which healthcare management information can be shared among various entities. This example is described in terms of the clinic 81 transferring records and information relating to one or more patients to a medical practice that will be seeing those patients. As further illustration and for ease of discussion and understanding, this process is described in terms of a particular example in which a medical practice is scheduled to see a plurality of patients on a given day and requests information and records for these patients from central repository. In this example, the medical office is an orthopedic medical practice, and clinic 81 is a hospital or other shared data management system maintaining patient records and information for a number of different patients who may be seen by different physicians, medical offices, or practices. It will become apparent to one of ordinary skill in the art how this process can be applied to other practices, practice types and operational scenarios.

Referring now to FIG. 10, at operation 424 clinic 81 pulls records corresponding to the patients that will be seen by the medical office for a specified time period. For example, the system can be configured to retrieve patient information for the medical office's daily patient schedule on a daily basis. Accordingly, in this example, the patient listing for that day can be provided to clinic 81 by the medical office so the clinic anyone knows which records to pull. As another example, scheduling information can be uploaded by the various medical offices or practices to clinic 81 as the appointments are scheduled (or in batches thereafter) and clinic 81 can be configured to store the schedule information and retrieve the patient information for the scheduled appointments without the need for a separate schedule to be sent from the medical offices to the clinic 81. As a further example, the data management system that clinic 81 can be configured to search the database for a listing of patients have an appointment scheduled for a particular medical office at a particular date. Clinic 81 can further be configured to retrieve patient records from the various data storage systems 88, 89, 90 (and any others) for each of the patients with a schedule appointment. Clinic 81 then can be configured to make this information available to front end 87 for communication to portal 82. In the example illustrated in FIG. 9, central data repository 71 places this information into temporary data storage 85 (e.g. a logical or physical data store such as a disk drive, folder or other storage space), which can be accessed by front end 87. Central data repository 71 can be further configured to include with these records information regarding which medical office the record should be sent to.

At operation 425, front end 87 retrieves the information from temporary data storage 85. In some embodiments, front end 87 can be configured to check data storage 85 periodically to determine whether there are any records that are ready for transfer. In another embodiment, central data repository 71 can be configured to alert front end 87 when records are placed in temporary data storage 85 and ready for transfer. For example, a patient management system can be configured to run at central data repository 71 to check patient schedules, pull patient files, and deliver appropriate records to temporary data storage 85 (or otherwise make them available for transfer to the medical office). In other embodiments, records can be flagged for transfer and front end 87 configured to periodically scan for flagged records. In some embodiments, flagging the records can include placing an instance of the records in a designation location (e.g., data storage 85) when they are ready for transfer. An instance of a record may be the original record, or it may be a copy.

At operation 430, front end 87 prepares and transfers the records to portal 82. In various embodiments, front end 87 can be configured to encrypt the records prior to transfer, perform any format conversion that may be needed, penetrate the clinic firewall, and transfer the records to portal 82.

At operation 433, portal 82 receives the records from central data repository 71 via interface 91. Portal 82 stores the records using data storage 92 and prepares the records for transfer to the medical office. In some embodiments, another layer of encryption can be added for data storage 92. The records received by portal 82 can be stored in storage 92 for a designated period of time. For example, in one embodiment, the records are stored for 30 days, after which time they are deleted. Portal 82 (e.g., communication management 93) can be further configured to determine the intended recipient (e.g. the designated medical office) of the records received. This information can be used by interface 91 to transfer the records to the appropriate medical office. In some embodiments, Portal 82 can be configured to receive, store and transfer a plurality of records from a plurality of different sources to one or more designated health care facilities. Portal 82 can, for example, provide virtual cloud storage and communications management to receive records from multiple sources, store the records, identify the appropriate recipients, group the records for transport and transport the records to the intended recipient.

At operation 435, interface 91 transfers the records to the medical office. Depending on its configuration, the medical office can be configured to receive the records at a front end system can further distribute them to one or more client devices 83, or it can be configured to receive the records directly into one or more client devices 83. Interface 91 can be configured to add another layer of encryption prior to sending the records to the medical office. Communication management 93 can oversee the communication process, manage the queuing of information, and check for an acknowledgment or confirmation from the medical office that the information was correctly received. If the knowledge meant does not come in an appropriate period of time, or if an error message is received, communication management 93 can cause the records to be retransmitted to the medical office. On the other hand, once confirmation is received that the records were successfully transferred, the communication management module 93 can delete the records from storage 92. In some embodiments, portal 82 is implemented as a cloud system and storage 92 as cloud storage. Accordingly, the one or more layers of encryption that can be applied to the data may be desirable to protect the integrity of the records in the cloud. Various encryption standards can be used including, for example, 128-bit military grade encryption to secure the data. In some embodiments, a cloud data service such as, for example, the CloudPrime Cloud Messaging product (available from CloudPrime at 300 Brannan St., San Francisco Calif., 94107) can be used to implement some or all of the functions of portal 82, front end 87, and interface 95.

At operation 438, the medical office receives the records. The medical office decrypts the records and checks their integrity. As shown in the example illustrated in FIG. 9, this can be done by an interface application 95. Interface application 95 can be an interface application at a front-end system at the medical office, or it can be an interface application that is separate from or part of one or more applications 73 running on a client device 83. Depending on the transfer process, and as indicated above, the records may be encrypted through one or more layers of encryption before they are received at the medical office. Accordingly, interface 95 can be configured to determine the levels and types of encryption applied decrypt information appropriately. Additionally, because the data types used by the various medical systems had clinic 81 may be different from the datatype expected by client device 83 (and indeed, different from system to system at clinic 81), interface 95 can further be configured to convert the datatype to that expected by client device 83, and more particularly to that expected by the applications 73.

At operation 440, interface 95 makes the records available to applications 73. Interface 95 can be configured to, for example, provide records of different types to the appropriate corresponding healthcare applications 98. In another embodiment, interface 95 can be configured to make the records available, and the healthcare applications 98 configured to retrieve records corresponding to their respective functions. For example, patient data and scheduling records and patient billing records can correspond to and be relevant to a treating physician's application, while billing records might correspond to a billing for Accounts Receivable application.

With the records available to the appropriate application or applications 98, the records can be accessed by the healthcare personnel, used in the care and treatment of the patients, and updated information can be entered into the applications 98 as appropriate. Completed or updated or annotated records, as well as new records can be created and uploaded to central data repository 71 (e.g., through portal 82) by the medical office. Accordingly, a temporary data storage folder 87 can be provided in which this information can be stored for transfer to the other entities by interface 95. Temporary data storage 87 can function in a manner similar to temporary data storage 85 at central data repository 71. That is, records can be stored in temporary data storage 87 with recipient or other routing information, retrieved by interface 95 and transferred.

Figure 11:
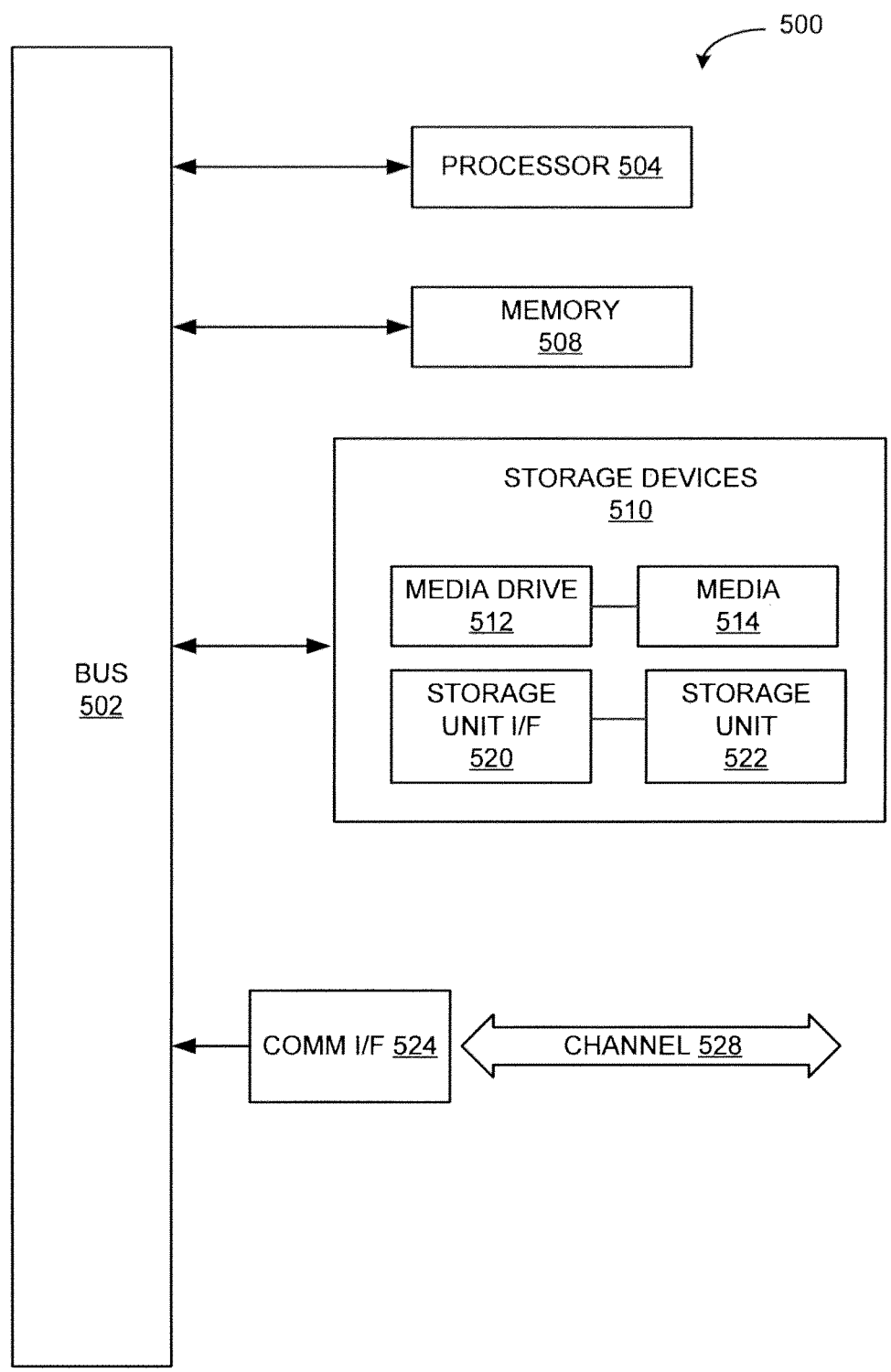
FIG. 11 illustrates an example computing module that may be used in implementing various features of embodiments of the disclosed technology.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 11. Various embodiments are described in terms of this example-computing module 500. After reading this description, it will become apparent to a person skilled in the relevant art how to implement the technology using other computing modules or architectures.

Referring now to FIG. 11, computing module 500 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random access memory (RAM) or other dynamic memory, might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a floppy disk drive, a magnetic tape drive, an optical disk drive, a CD or DVD drive (R or RW), or other removable or fixed media drive might be provided. Accordingly, storage media 514 might include, for example, a hard disk, a floppy disk, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A method to manage records and data in an orthopedic care practice, the method being implemented in a computer system including one or more physical processors and electronic nonvolatile data storage memories coupled to a network, the method comprising:
   programming a server that is connected to the network to receive over the network and store in a nonvolatile data storage memory a set of individual data records of disparate form and format, wherein the set of individual data records comprises patient identification data for a plurality of patients scheduled for appointments at the orthopedic care practice in a time window, patients' health data, and further comprising inventory data;
   further programming the server to access and retrieve from the data storage memory patient data for the plurality of patients having an appointment during the time window, to translate the patient data to a form and format for an app at a client computing device at a check-in location, and communicating over the network the schedule of appointments in the time window to the check-in client computing wherein the app at the check-in client computing device programs the client computing device to receive the schedule and to control a display screen on which the schedule is displayed, and
   further programming the server to also translate the retrieved patient data for the plurality of patients having an appointment during the time window to a form and format for use by an app in a first hand-held computing device, to communicate the schedule of patient appointments to the first hand-held computing device which is associated with a healthcare practitioner ("HCP"), the schedule showing the patient identifications for the plurality of patients scheduled and an appointment time corresponding to each patient, the displayed schedule including a listing of entries for a subset of the appointments scheduled at the healthcare facility in the time window, wherein the HCP hand-held computing device includes a network interface coupled to the network;
   checking in a patient for an appointment at the orthopedic care practice at the check-in client computing device, comprising the steps of:
      identifying the patient and confirming the patient's name is on the list of patients having an appointment in the time window;
      reviewing additional patient information as a gatekeeping function to determine if the patient has met certain requirements so that the scheduled appointment can be approved, including at least one of reviewing current insurance information for valid insurance of the patient, verifying that co-payment has been made, verifying that a prior test on the patient has been completed, and verifying that a prior healthcare practitioner examination of the patient has been completed before a scheduled test can be performed on the patient;
      locking the appointment of a patient if review of the additional patient information indicates that the patient has not met one of the requirements and therefore the scheduled appointment is not approved and communicating the locked appointment to the server for storing in the data storage memory;
   linking a schedule entry for a first appointment of the schedule to at least part of a first health record stored on the data storage memory that corresponds to a first patient associated with the first appointment by the app of the first HCP hand-held computing device;
   receiving a first user input from a healthcare practitioner by the app at the first HCP hand-held computing device selecting the first patient or the first appointment that is displayed on the schedule displayed on the hand-held computing device for examination;
   in response to receiving the first user input, the app at the first HCP hand-held computing device is programmed to display a link to at least part of the first health record if the appointment has been approved, or showing the appointment as locked until approval of the appointment is granted;

receiving a second user input at the app of the first HCP hand-held computing device from a healthcare practitioner as to examination of the selected patient, the second user input selecting the link to at least part of the first health record;

in response to receiving the second user input, the app of the first HCP hand-held computing device programs the first HCP hand-held computing device to retrieve over the network from the data storage memory, via the network interface coupled to the network and to store the examination of the selected patient in the data storage memory;

receiving a third user input at the app of the first HCP hand-held computing device from a healthcare practitioner, the third user input including a prescription for an orthopedic brace for the first patient associated with the first appointment;

transmitting from the app of the first HCP hand-held computing device to an app of a second HCP hand-held computing device the orthopedic brace information with a key code to allow a second healthcare practitioner to access to inventory storage to obtain the prescribed brace for the patient, wherein the app of the second HCP hand-held computing device includes a network interface coupled to the network and the app transmitting to the server that the brace has been obtained for the patient;

receiving a fourth user input from the app of the second HCP hand-held computing device indicating that the orthopedic brace has been fitted to the patient and delivered to the patient;

transmitting to the server for storing in the data storage memory, via the network interface of the second HCP hand-held computing device coupled to the network, the fitting information and the delivery information of the orthopedic brace to the patient to update the patient's health data in the data storage memory; and in the event that the brace did not fit the patient, returning the brace to inventory storage and wherein the app of the second HCP hand-held computing device communicates to the server to revise the inventory data and the patient health data to show that the brace has been returned;

wherein all apps of the HCP hand-held computing devices communicate in the same form and format of data for the communications recited herein and the server is programmed to communicate with all apps of the HCP hand-held computing devices in that form and format of data and to translate all disparate data types into that form and format.

2. The method of claim 1, wherein the individual data records further comprise at least one of patient management system records and patient billing system records.

3. The method of claim 1, wherein the individual data records further comprise data relating to an outcome of prescribed follow-on care.

4. The method of claim 1, wherein the apps of the check-in device and the first HCP hand-held computing device are further programmed to sort the schedule by at least one of attending physician, appointment time, and treatment room.

5. The method of claim 1, wherein the method further comprises the app programming the second HCP handheld computing device to create an order record, the order record comprising information about the order for the prescribed orthopedic brace, and to communicate that order record to the server for storage in the data storage memory.

6. The method of claim 1, further comprising programming the server for accepting from the app of the second HCP handheld computing device input confirming delivery of the prescribed orthopedic brace to the patient associated with the first appointment and storing the input in a patient file on the data storage memory.

7. The method of claim 1, further comprising programming the server to update on the data storage memory inventory records to reflect that the prescribed orthopedic brace has been removed from inventory.

8. The method of claim 6, further comprising programming the server to create a patient billing record to reflect that the prescribed orthopedic brace has been delivered to the patient associated with the first appointment.

9. The method of claim 1, wherein the server is further programmed for:

accepting a fifth user input at an app of the second HCP handheld computing device from a healthcare practitioner, the fifth user input entering treatment information comprising information pertaining to an examination of the patient associated with the first appointment;

updating the patient's health data to reflect the treatment information; and storing, in the data storage memory, at least part of the updated first health record.

10. The method of claim 1, wherein the other healthcare practitioner comprises a physician's assistant.

* * * * *